(12) United States Patent
Angelescu et al.

(10) Patent No.: US 7,575,681 B2
(45) Date of Patent: Aug. 18, 2009

(54) MICROFLUIDIC SEPARATOR

(75) Inventors: Dan Eugen Angelescu, Danbury, CT (US); Philippe Salamitou, Paris (FR); Joyce Wong, Pasadena, CA (US); Bhavani Raghuraman, Wilton, CT (US); Brian Oliver Clark, Sugar Land, TX (US)

(73) Assignee: Schlumberger Technology Corporation, Ridgefield, CT (US)

( * ) Notice: Subject to any disclaimer, the term of this patent is extended or adjusted under 35 U.S.C. 154(b) by 814 days.

(21) Appl. No.: 10/935,858

(22) Filed: Sep. 8, 2004

(65) Prior Publication Data
US 2006/0008913 A1    Jan. 12, 2006

(51) Int. Cl.
*B01D 63/00* (2006.01)
*B01L 11/00* (2006.01)

(52) U.S. Cl. .................. 210/321.74; 210/321.6; 210/257.2; 422/101; 166/308.3

(58) Field of Classification Search ............. 210/321.6, 210/321.75, 257.2; 422/100–102, 64, 68, 422/72; 435/63, 45; 166/308.3, 380, 302
See application file for complete search history.

(56) References Cited

U.S. PATENT DOCUMENTS

| | | | |
|---|---|---|---|
| 5,116,759 A | 5/1992 | Klainer et al. ............ 435/288 |
| 5,984,023 A | 11/1999 | Sharma et al. ............ 175/50 |
| 7,264,723 B2 * | 9/2007 | Singh et al. ............ 210/321.6 |
| 7,323,140 B2 * | 1/2008 | Handique et al. ......... 422/68.1 |
| 7,332,126 B2 * | 2/2008 | Tooke et al. ............ 422/64 |
| 7,351,376 B1 * | 4/2008 | Quake et al. ............ 422/100 |
| 7,378,280 B2 * | 5/2008 | Quake et al. ............ 436/63 |
| 7,390,463 B2 * | 6/2008 | He et al. ............ 422/102 |
| 2002/0187074 A1 | 12/2002 | O'Connor et al. ......... 422/82.05 |
| 2003/0106799 A1 | 6/2003 | Covington et al. ......... 204/600 |
| 2003/0150791 A1 | 8/2003 | Cho et al. ............ 210/321.84 |
| 2004/0129874 A1 | 7/2004 | Torgersen et al. .......... 250/255 |

FOREIGN PATENT DOCUMENTS

| | | |
|---|---|---|
| DE | 19941271 A1 | 4/2001 |
| EP | 1614465 A1 * | 4/2005 |
| JP | 2003190768 A | 7/2003 |

(Continued)

OTHER PUBLICATIONS

Combined Search and Examination Report Under Sections 17 and 18(3) from the United Kingdom Patent Office for Application GB0518160.7, date of search Nov. 30, 2005.

(Continued)

*Primary Examiner*—Ana M Fortuna
(74) *Attorney, Agent, or Firm*—Jody Lynn DeStefanis; William Batzer; James McAleenan

(57) ABSTRACT

The present invention provides methods and apparatus for separating and/or analyzing fluids of interest. According to principles of the present invention, fluid analysis is accomplished with microfluidic devices and may be reported in real-time or near real-time in a subterranean environment. In addition or alternative to oilfield applications, the principles of the present invention contemplate separation in a laboratory or other environment for biological sample separation and analytical chemistry applications. The present invention is capable of separating liquid-liquid mixtures or emulsions in a microfluidic device without fouling.

16 Claims, 5 Drawing Sheets

FOREIGN PATENT DOCUMENTS

| WO | WO 00/20117 A2 | 4/2000 |
| WO | WO 00/20117 A3 | 4/2000 |
| WO | 02/77613 A2 | 3/2002 |
| WO | 2004/087283 A1 | 3/2004 |

OTHER PUBLICATIONS

Manz et al. "Miniaturized Total Chemical and Analysis Systems: A Novel Concept for Chemical Sensing". *Sensors and Actuators* B, vol. B1 (1990), pp. 244-248.

McDonald, J. C. et al. "Fabrication of Microfluidic Systems in Poly(dimethylsiloxane)". *Electrophoresis*, vol. 21 (2000), pp. 27-40.

Ocean Optics. "Fiber Optic pH Sensors". *Product Catalog on Spectrometers and Accessories* (2004), p. 58.

Strook et al. "Chaotic Mixer for Microchannels". *Science*, vol. 295, (2002), pp. 647-651.

Terry, S. C. "A Gas Chromatography System Fabricated on a Si Wafer Using Integrated Circuit Technology". *PhD Thesis*, Stanford University, (1975).

Tirmizi, N. P. et al. "Demulsification of Water/Oil/Solid Emulsions by Hollow-Fiber Membranes". *A.I.Ch.E. Journal*, vol. 42, No. 5 (1996), pp. 1263-1276.

Tsai, Jr. H. et al. "Active Microfluidic Mixer and Gas Bubble Filter Driven by Thermal Bubble Micropump". *Elsevier, Sensors and Actuators*, vol. A, (2002), pp. 665-671.

Verpoorte et al. "Microfluidics Meets MEMS". *Proceedings of the IEEE*, vol. 91, No. 6 (Jun. 2003), pp. 930-953.

Vogel, A. I. *Text-Book of Quantitative Inorganic Analysis, 3rd Edition*, John Wiley and Sons, Inc. (1961), Chapter 10-12.

\* cited by examiner

MICROFLUIDIC SEPARATOR

This patent application claims priority from U.S. patent application Ser. No. 10/885,471 filed Jul. 6, 2004 pending, incorporated by reference herein in its entirety.

FIELD OF THE INVENTION

The present invention relates to chemical analysis and, more particularly, to the separation of fluids in microfluidic systems.

BACKGROUND

The ability to reliably separate a fluid of interest can be very beneficial for oilfield, medical, biological, and analytical chemistry applications. Fluids of interest may include water, oil, gas, or other fluids. Separating fluids of interest enables specific measurements to be performed on the particular fluid. For example, pH and various ion concentrations may be measured if the fluid of interest is water. For oil, near-infrared absorption spectroscopy may be performed to detect various light-weight hydrocarbons, and other types of chromatography may be used to detect detailed chemical composition.

However, in order to perform accurate measurements on the fluid of interest, the fluid of interest must be separated from other components prior to taking the measurements. The separation methods conventionally used in the oilfield include gravity separation, centrifugation, and hydrocyclone separation. Conventional methods are used to separate large quantities (i.e. for production purposes) and have several drawbacks. One drawback of conventional separation techniques is the time it takes to perform them. Conventional separation techniques often take a long time, depending on the particular composition of the fluid. For example, a fine emulsion may take months to separate by gravity, although a simple mixture may take only a few minutes. Another drawback of conventional separation techniques is poor separation performance. Conventional separation techniques usually do not perform a complete separation. There are almost always traces of contaminants in the sample fluid of interest.

In addition, in most oilfield applications, analyses of formation fluids of interest are typically performed at the surface adjacent to the well or in a remote laboratory environment. However, bringing sample fluids to the surface, transporting them to a laboratory, and separating the phase mixtures is time consuming, cost inefficient and provides only post-factum information. Moreover, fluid samples collected downhole can undergo various reversible and irreversible phase transitions between the point of collection and the point of laboratory analysis as pressure and temperature conditions change.

Recently, biologists and analytical chemists have started to perform analysis of various fluids in laboratories on a micro-scale. The analysis of minute fluid amounts is accomplished with various microfluidic and/or MEM (Micro Electro-Mechanical) systems. Microfluidic systems or devices are typically comprised of fluidic channels with lateral dimensions ranging from tens to hundreds of micrometers and are designed to operate with extremely small volumetric flow rates. However, similar to analysis on a macro-scale, at the micro-scale it is equally necessary to separate the fluid of interest from other fluids in order to perform an effective analysis. Prior to a co-pending patent application Ser. No. 10/885,471 filed Jul. 6, 2004 and entitled "Microfluidic System for Chemical Analysis," which is hereby incorporated in its entirety by this reference, microfluidic devices for oilfield applications have only been suitable for use in laboratory environments.

Accordingly, there is a need for a microfluidic separator capable of separating emulsions, liquid-liquid and liquid-gas mixtures in any environment, including uphole and downhole oilfield environments. There is also a need for a microfluidic separator which is addressable remotely from surface in oilfield environments.

SUMMARY OF THE INVENTION

The present invention addresses the above-described deficiencies and others. Specifically, the present invention provides methods and apparatus for separating and/or analyzing fluids of interest. According to principles of the present invention, fluid analysis is accomplished with microfluidic devices and methods and may be reported in real-time or near real-time from a subterranean environment.

One aspect of the present invention provides a fluid separation method. The method comprises separating a multiphase mixture with a membrane in a microfluidic device. The method may also include maintaining a pressure difference across the membrane below a capillary break-through pressure of a nonwetting component of the multiphase mixture. The method may include inserting the membrane and the microfluidic device into a subterranean oilfield environment. Thus, the separation may comprise separating the multiphase mixture in a wellbore, while drilling (MWD), during wireline operations, or during permanent production logging. The separation may also be done at a surface location. According to some aspects, the separation further comprises flowing the multiphase mixture across the membrane in a direction substantially parallel to the membrane. The separation method may include flowing one phase of the multiphase mixture through pores of the membrane. The separation may comprise separating one liquid of the multiphase mixture from another liquid or gas, or separating a gas from a liquid of the multiphase mixture. A pressure differential may be created across the membrane in the microfluidic device to facilitate separation.

According to some aspects, the membrane may be a water-repellant, oil-permeable membrane; an oil-repellent, water-permeable membrane; an oil-and-water-repellent gas permeable membrane, or other membrane. A liquid of interest from the multiphase mixture may flow through the membrane at a flow rate at least one-to-two orders of magnitude lower than a flow rate of the multiphase mixture passing by the membrane. The separation may comprise passing a liquid of interest from the multiphase mixture through the membrane and preventing the membrane from fouling without back-flushing. After separation, the fluid of interest may pass into an H-fractal fluid channel configuration.

According to another aspect of the invention, a fluid separation method comprises separating a first liquid in a multiphase mixture from a second liquid in the multiphase mixture with one of a membrane or a plurality of microfabricated pores in a microfluidic device. The membrane and the microfluidic device may be inserted into a subterranean oilfield environment. Thus, the separating may comprise separating the first liquid in a wellbore. The separating may also comprise part of: a measurement while drilling operation, a wireline operation, or a permanent production logging operation.

Another aspect of the invention provides a method of testing a subterranean fluid in situ. The method includes separating a liquid of interest from another liquid downhole in a microfluidic device, passing the separated liquid of interest into a microfluidic analyzer, analyzing the liquid of interest, and reporting the analysis uphole in near real-time. The analysis may comprise continuously passing a new supply of the separated liquid of interest into the microfluidic analyzer. The analyzing may comprise passing a new supply of the separated liquid of interest at different depths in a wellbore during a drilling or wireline logging operation, or during permanent monitoring.

The present invention also provides an apparatus, including a microfluidic device comprising a porous membrane for separating a multiphase mixture. The microfluidic device may be surrounded by a submersible housing. The membrane may be a hydrophobic membrane, an oleophobic membrane, a hydrophobic/oleophobic gas permeable membrane, or some other separation membrane. The membrane may comprise PTFE, polyethylene, polypropylene, nylon, or other materials. The apparatus may include a microsieve adjacent to and downstream of the membrane. The porous membrane may be mechanically connected or adhesively connected to the microsieve. Various chemical modifications may be performed on the porous membrane in order to increase its adhesive properties. The apparatus may include a downhole oilfield tool having a fluid flow stream, such that the microfluidic device is disposed in the fluid flow stream and the porous membrane is arranged substantially tangent to a flow direction of the fluid flow stream. The microfluidic device may have a sample manipulation/analysis module or chip. The microfluidic device may also include a capillary gas separator downstream of the porous membrane. The capillary gas separator may comprise microfabricated channels arranged substantially tangent to a fluid stream downstream of the porous membrane. The microfabricated channels may comprise pores of approximately 10 microns or less. The microfluidic device may include a secondary fluid outlet channel tangentially downstream of the capillary gas separator, and an oil outlet downstream of the capillary gas separator.

Another embodiment of the present invention comprises a microfluidic system for performing fluid analysis comprising a submersible housing having a fluid analyzer and a power supply to provide power to said system, a substrata for receiving a multiphase mixture through a fluid sample inlet, wherein the substrate interconnects with the housing, and a membrane disposed across the fluid sample inlet for separating a fluid of interest from the multiphase mixture.

Another aspect of the invention provides a method of separating a multi-phase mixture, comprising: sending the multi-phase mixture containing a fluid of interest through a microfluidic channel in contact with a membrane wet by one or more non-fluids of interest contained in the mixture, permeating the one or more non-fluids of interest through the membrane, and leaving a stream of the fluid of interest to flow to an outlet of the channel.

Another aspect of the invention provides a method of separating a multi-phase mixture of two or more immiscible fluids, comprising: sending the multi-phase mixture through a first microfluidic channel in contact with a membrane wet by a first of the two or more immiscible fluids, passing the first fluid through the membrane, collecting the first fluid in a second microfluidic channel, directing the first fluid to an outlet of the second microfluidic channel, and leaving a second of the two or more immiscible fluids to flow to an outlet of the first microfluidic channel. The method may further include analyzing the first and second fluids.

Additional advantages and novel features of the invention are set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate preferred embodiments of the present invention and are a part of the specification. Together with the following description, the drawings demonstrate and explain the principles of the present invention.

DETAILED DESCRIPTION

Figure 1:
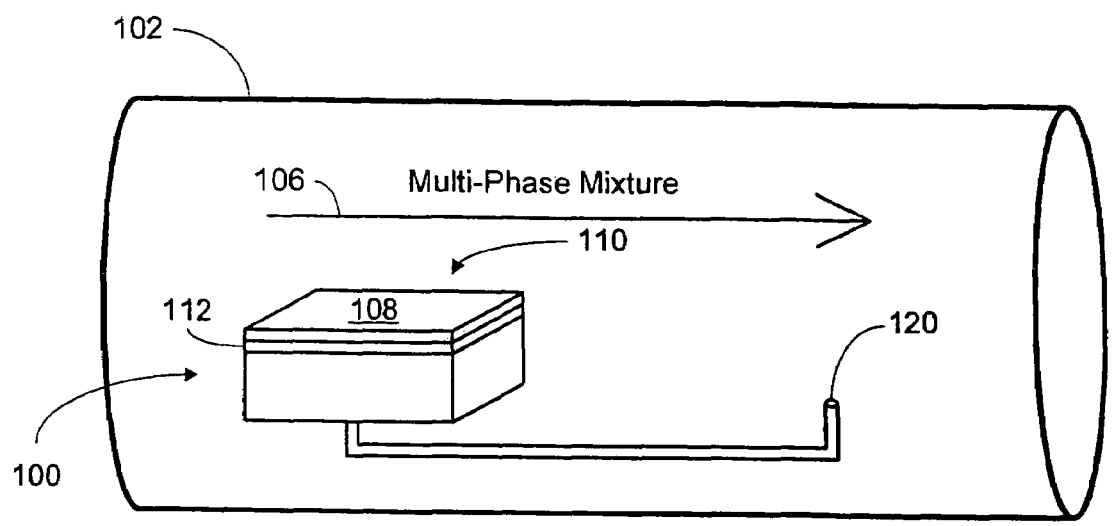
FIG. 1 is a schematic diagram of a sample tool with a microfluidic device and a separator according to one embodiment of the present invention.

Illustrative embodiments and aspects of the invention are described below. It will of course be appreciated that in the development of any such actual embodiment, numerous implementation-specific decisions must be made to achieve the developers' specific goals, such as compliance with system-related and business-related constraints that will vary from one implementation to another. Moreover, it will be appreciated that such a development effort might be complex and time-consuming but would nevertheless be a routine undertaking for those of ordinary skill in the art having the benefit of this disclosure.

The present invention contemplates methods and apparatus for separating multiphase mixtures including liquid-gas mixtures, liquid-liquid mixtures, and emulsions, especially in microfluidic devices. As mentioned in the background, in many applications, including oil well evaluation and aquifer management, fluid samples must be separated and analyzed. The principles described herein facilitate separation of liquid-liquid mixtures and liquid-gas mixtures. The separation according to the present invention may take place in a downhole environment during wireline operations, while drilling (Logging While Drilling (LWD)/Measurements While Drilling (MWD)), during permanent production logging, and is not limited to laboratory conditions. However, the principles described herein may be used at a surface or laboratory location as well. Application of the principles of the present invention may be used, for example, to provide continuous real-time or near real-time data concerning formation fluid in a subterranean formation.

As used throughout the specification and claims, the terms "microfluidic system" or "microfluidic device" mean a network of one or more channels with dimensions of tens to hundreds of micrometers that may have one or more components including, but not limited to: pumps, valves, mixers, integrated optical fibers, and other components integrated on a chip for the purpose of manipulating and/or analyzing minute amounts of fluid. The term "tangentially downstream" refers to a fluid stream, a portion of which is flowing by, rather than through, a stated component. "To foul" means to become clogged, obstructed, or blocked. "Fluid" means a continuous, amorphous substance whose molecules move freely past one another and that has the tendency to assume the shape of its container, including both liquids and gases. In the context of membranes, "hydrophobic" is the property of a material of not being wet by water (water impermeable). "Hydrophilic" is the property of being wet by water (water permeable). "Oleophobic" means not wet by oil (oil impermeable) and "oleophilic" means wet by oil (oil permeable). "Microsieve" refers to a network of microchannels in contact with a membrane used for collecting a fluid of interest permeating through a membrane. The words "including" and "having," as used in the specification, including the claims, have the same meaning as the word "comprising."

While the present invention is described herein according to certain particular embodiments and may be well suited to oilfield applications, the present invention is not so limited. The principles of the present invention may be extended to any application wherein multi-phase separation may be useful. For example, the principles of the present invention may be applied to biological samples, chemical samples, or any other microfluidic samples and are not limited to oilfield applications.

Many types of small-scale sensors are currently being considered in the oil industry, in particular for performing measurements in downhole environments. Miniaturized sensors capable of monitoring pressure, density, viscosity, and temperature are currently being developed and used. There are several reasons behind this trend toward miniaturization, including reduced fabrication costs (such sensors can be batch-produced), smaller size (a sensitive parameter given the limited space available in the downhole environment), and lower power consumption. In addition, using miniaturized sensors such as a fluid analyzer in accordance with principles of the present invention, measurements typically involving large lab equipment may instead be performed downhole in the natural environment.

Among the properties that could not be fully characterized downhole prior to the present invention is the chemical composition of the various fluids extracted from the formation. As mentioned in the background, one obstacle to downhole chemical analysis is efficiently separating phases (e.g. oil, water, gas, particulates, contamination from drilling muds, etc.). Filtering usually fails due to filter fouling, and gravitational separation based on density mismatch is extremely slow. Accelerated separation methods such as centrifugation and hydrocyclone separation are difficult to implement and impractical in a downhole environment.

Therefore, according to the present invention, a microfluidic device or system 100 shown in FIG. 1 includes a multi-phase separator that may be used in downhole environments without the tendency to foul. The description that follows includes a discussion of apparatus according to principles of the present invention, followed by a description of microfluidic and microanalysis systems in general, and an explanation of methods of practicing the invention.

FIG. 1 illustrates a sampling tool 102 in fluid communication with formation fluid mixtures. An intended flow direction of fluids with respect to the sampling or drilling tool 102 is represented by an arrow 106.

Figure 2:
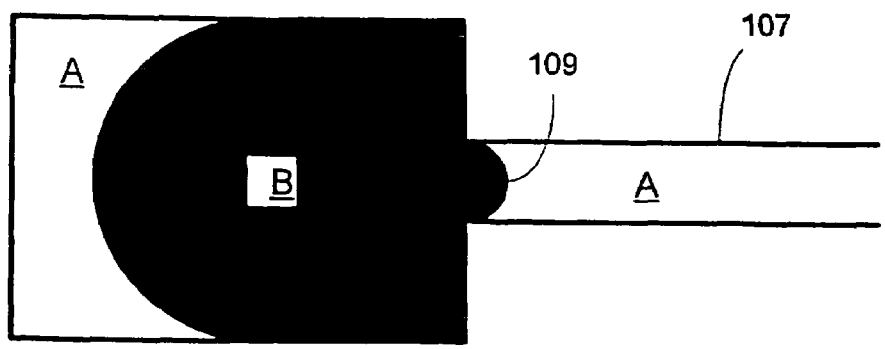
FIG. 2 is a representative diagram illustrating wetting properties of two different fluids with respect to a pore.

According to principles of the present invention, the multi-phase separator of the microfluidic device 100 shown in FIG. 1 relies on differences in wetting behavior between various fluids on certain materials and microstructures in order to perform separation of the multi-phase fluids. Certain materials and microstructures contain pores or capillaries which are wetted by certain fluids but not by others. For example, referring to FIG. 2, a pore 107 is wet by Fluid A but not by Fluid B. Therefore, Fluid A flows freely through the pore 107 whereas the nonwetting Fluid B forms a meniscus 109 which prevents Fluid B from entering the pore 107. If pressure applied across the pore 107 becomes larger than a certain breakthrough pressure, Fluid B will enter the pore 107. However, if the pressure of Fluid B is maintained below the breakthrough pressure, only Fluid A will flow through the pore.

The magnitude of the breakthrough pressure of a fluid depends on the surface properties (such as surface energy) of the material that incorporates the pores, the dimensions of the pore (such as diameter), and the surface tension of the two immiscible fluids and of their interface (e.g. Fluids A and B).

Returning to FIG. 1, the multi-phase separator comprises microfabricated channels or a porous membrane 108 disposed at or across a fluid sample inlet 110. The porous membrane 108 preferably has high porosity and submicron pore size. Therefore, the porous membrane 108 provides both capillary separation of a fluid of interest (such as oil) from a secondary fluid or liquid (such as water), and particulate filtering. According to the embodiment of FIG. 1, the membrane 108 may be made of hydrophobic, oleophilic material; hydrophilic, oleophobic material, or a material that is gas permeable and both hydrophobic and oleophobic. Other materials may also be used. The membrane 108 is capable of liquid-liquid separation and/or gas-liquid separation without fouling. The membrane 108 is preferably made of a suitable chemically and thermally resistant material, such as PTFE (polytetrafluroethylene, known under the brand name of Teflon®) for Goretex® or Porotex® membranes, polyethylene/polypropylene for Celgard® membranes, nylon, or other material.

The membrane 108 is preferably placed across the inlet 110 adjacent to a microsieve 112. Nevertheless, the membrane 108 may be located anywhere between the inlet 110 and an outlet 120. The microsieve 112 is optional. However, the microsieve 112 provides a support or backing to the membrane 108 and creates a uniform distribution of pressure over the entire area of the membrane 108. The microsieve 112 is preferably integrated with the microfluidic system 100 and may comprise a wire mesh or closely perforated plate. The membrane 108 may be mechanically connected to the microsieve 112. The mechanical connection between the membrane 108 and the microsieve 112 may be achieved according to some embodiments by pressing the membrane 108 with an o-ring or other fastener, or it may be adhesively attached. Chemical modifications may be performed on the membrane material in order to improve its adhesive properties. The membrane 108 is preferably in direct contact with the microsieve 112, minimizing dead-volume issues which can become problematic in low flow rate regimes.

As shown in FIG. 1, the assembly comprising the membrane 108 and microsieve 112 is preferably arranged substantially tangent to or parallel with the intended flow direction 106 of fluids flowing through or along the sampling tool 102. Furthermore, the flow rate through the membrane 108 is extremely low, on the order of several microliters per minute, which corresponds to a very low pressure drop across the membrane 108. The pressure drop across the membrane 108 is preferably maintained well below the pressure necessary for capillary break-through of the nonwetting fluid. The configuration of the membrane 108 disposed substantially in a tangent or cross-flow direction with respect to the fluid advantageously results in self-cleaning of the membrane 108. The flow rate across or passing by the membrane 108 is at least one-to-two, and preferably several, orders of magnitude larger than the flow rate through the membrane 108. Therefore, cake build-up and fouling problems are prevented, eliminating the need to backflush.

Figure 3:
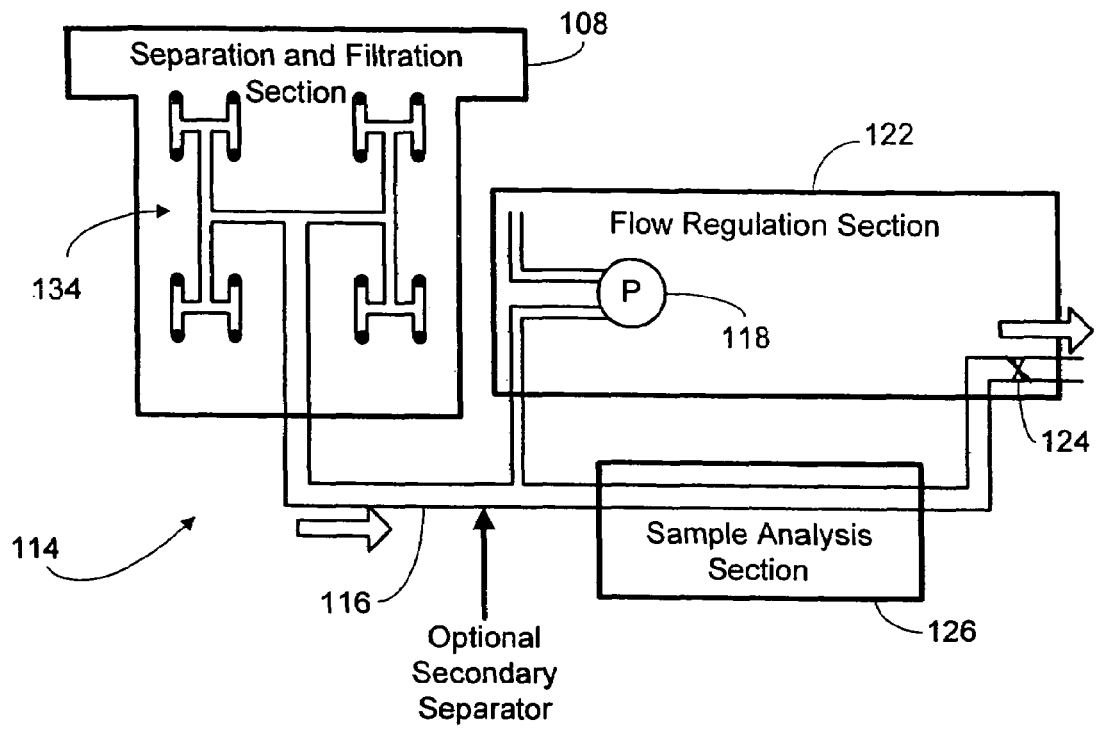
FIG. 3 is a block diagram illustrating details of the microfluidic device and separator of FIG. 1 according to one embodiment of the present invention.

The membrane 108 and microsieve 112 assembly may be connected to or integral with the microfluidic system 100, which, according to the schematic embodiment of FIG. 3, is a microfluidic sample manipulation/analysis sensor chip 114. As shown in FIG. 3, the microfluidic sensor chip 114 is configured to manipulate and analyze microscopic (few microliters and smaller) amounts of fluid. Suction pressure to assure flow through the membrane 108, microsieve 112 (FIG. 1), and the channels 116 disposed in the chip 114 may be generated either actively or statically. According to FIG. 3, a pressure gauge 118 may monitor the pressure drop across the membrane 108 of the chip 114. One or several valves 124, possibly in conjunction with a micropump, may be used in order to maintain the pressure drop below the breakthrough pressure of the nonwetting phase, as part of a flow regulation system 122. However, according to other embodiments, an inherent flow-generated pressure drop inside a wellbore or oil pipe between the inlet 110 (FIG. 1) and an outlet 120 (FIG. 1) of the microfluidic sensor chip 114 may provide the suction pressure.

Figure 4:
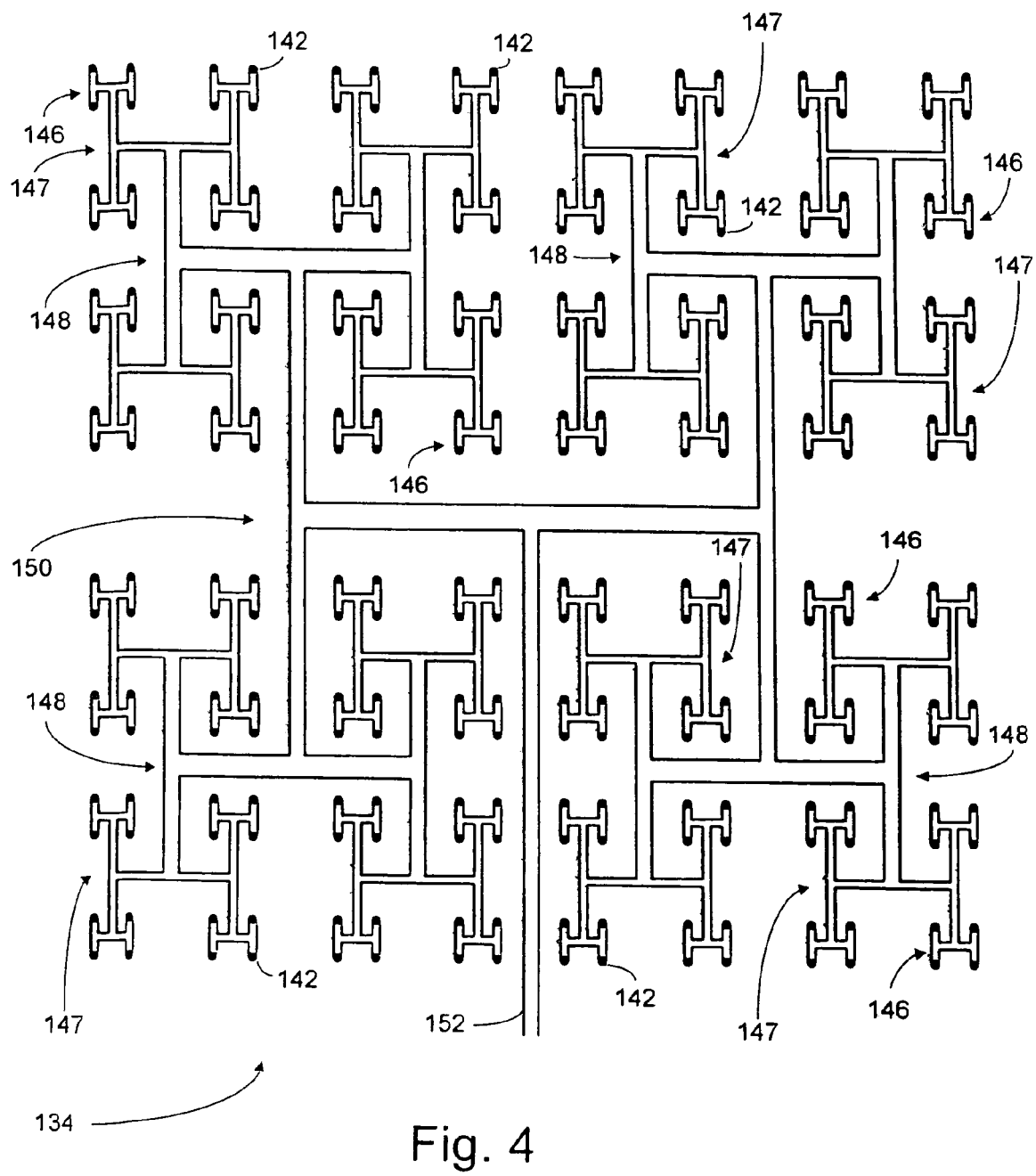
FIG. 4 is an illustration of an H-fractional microfluidic channel arrangement according to one embodiment of the present invention.

As a fluid of interest such as liquid oil passes through the membrane 108, it enters an interconnected arrangement of collection channels. According to the embodiment of FIG. 3, the collection channels comprise an H-fractal configuration 134. FIG. 4 illustrates details of the H-fractal configuration. As shown in FIG. 4, the collection channels comprise a plurality of nodes 142, four nodes for each of a plurality of first H's 146. Fluid may enter the configuration 134 at each of the nodes 142. Each of the first H's 146 is in fluid communication with adjacent first H's 146 to form a second set of H's 147. According to the embodiment shown, a set of four adjacent first H's 146 cooperate to form a second H 147. Likewise, each of the plurality of second H's 147 is in fluid communication with one another to create a third plurality of H's 148. According to the embodiment shown, four of the second plurality of H's 147 cooperate to form a third H 148. Each of the third plurality of H's 148 is in fluid communication with one another to create a fourth H 150. The pattern shown in FIG. 4 may obviously be expanded or contracted as desired. The fourth H 150 is in fluid communication with a fluid outlet channel 152, which feeds into the channel 116 shown in FIG. 3. One advantage of the H-fractal configuration is an equidistant fluid path length between each node 142 and the fluid outlet channel 152. Therefore, regardless of what node 142 a volume of fluid enters, all volumes of fluid entering the different nodes 142 at the approximate same time will also reach the fluid outlet channel 152 at substantially the same time, improving the response time of the system. In addition, this configuration may also improve the uniformity of fluid sampling across the filter.

The fluid outlet channel 152 may feed a sample analysis section 126 of the chip 114 shown in FIG. 3. The functions of the sample analysis section 126 are discussed in more detail below. However, there may also be an intermediate or secondary separator through which sample fluid flows before entering the sample analysis section 126 as discussed below.

According to some embodiments, the membrane 108 separates fluids such as liquids of interest (e.g. oil) from other fluids (which may be liquids such as water). In addition, the membrane 108 is capable of separating liquids of interest from gases. However, it is possible that some gas may be dissolved in the liquid of interest as it passes through the membrane 108. Bubbles may form from the dissolved gas due, for example, to the differential pressure across the membrane 108. Therefore, according to some embodiments, a second separator, which is preferably a liquid-gas separator, may be arranged downstream of the membrane 108.

Figure 5:
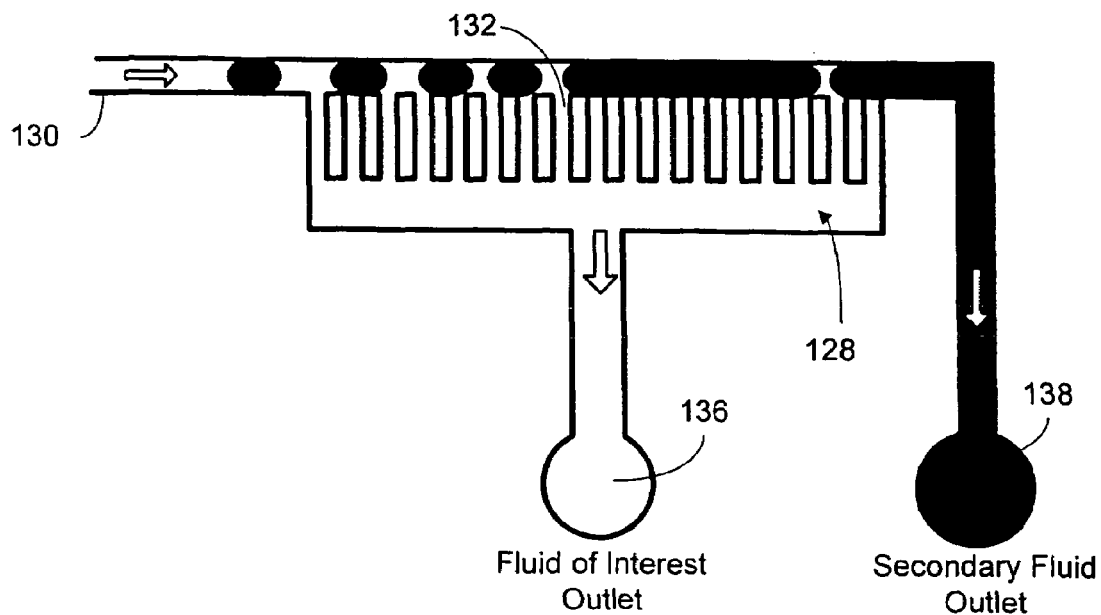
FIG. 5 is a schematic diagram illustrating a second separator that may be combined with the separator shown in FIGS. 1-2 according to one embodiment of the present invention.

According to the embodiment of FIG. 5, the second separator is a capillary gas separator comprising a plurality of microfabricated pores such as microfabricated filter 128. The microfabricated filter 128 is optional, but may, however, replace the membrane 108 and function as a primary fluid separator. As shown in FIG. 5, the microfabricated filter 128 is arranged substantially tangent to a fluid stream flowing through a channel 130 downstream of the porous membrane 108 (FIG. 1). Microfluidic channels such as the channel 130 that transports emulsions or other fluids may be tens to hundreds of microns wide and deep. On the other hand, the microfabricated filter 128 preferably comprises pores such as hydrophobic, oleophilic pores; or hydrophilic, oleophobic pores 132 on the order of approximately 10 microns or less. Only the fluid of interest (that wets the pore material) passes through the pores 132, while other fluids (such as water in the case of hydrophobic pores) tend to flow tangentially past the filter 128.

The fluid of interest passes through the microfabricated filter 128 as a single phase to the sample analysis section 126 (FIG. 3), where it is manipulated and/or analyzed and discharged through an outlet 136. The secondary fluid and any separated phases pass by the microfabricated filter 128 and eventually out of the microfluidic device 100 through a secondary fluid outlet 138.

The single phase samples of the fluid of interest (which may be, for example, oil, water, gas, biological fluids, etc.) may undergo one or more of several possible analyses in the sample analysis section 126 (FIG. 3). For example, the sample analysis section 126 (FIG. 3) may perform functions including, but not limited to: gas chromatography, mass spectroscopy, titration, visible/infrared absorption spectroscopy, fluorescence detection, resistivity measurements, and physical measurements such as pressure, density, viscosity, and temperature. As discussed below, these functions can be built into the sample analysis section 126 (FIG. 3) according to conventional methods by those of skill in the art having the benefit of this disclosure.

According to some aspects of the invention, fluid may pass into or through the microfluidic system 100 (FIG. 1) once, at intervals, or even continuously to monitor properties (and contamination) of a phase of interest and provide real-time data uphole. The microfluidic system 100 (FIG. 1) may include components such as those described in co-pending patent application Ser. No. 10/885,471 filed Jul. 6, 2004 to facilitate remote downhole use.

Microfluidic systems such as the microfluidic system 100 discussed with reference to FIGS. 1-5 can be constructed using standard microfabrication techniques by those of skill in the art having the benefit of this disclosure. For example, the microfluidic system 100 may be fabricated in silicon and bonded to Pyrex® glass or sapphire. Sapphire may be particularly useful due to its good chemical and thermal resistance and excellent optical properties. Having the benefit of this disclosure, the technologies for constructing the microfluidic system 100 are well established and available from numerous commercial and university foundries. In addition, the microfluidic system 100 of the present invention may be constructed using soft lithography (micromolding of an appropriate elastomer, typically silicone-based), using micromolding of various plastic materials or curing certain resins inside pre-made molds.

As mentioned above, flow through the microfluidic system 100 may be actively generated by micro-pumps, which are available from several manufacturers including ThinXXS of Zweibrucken, Germany, and Micropump of Vancouver, Wash. Various valve types (integrated or exterior) commercially available can also be employed to regulate flow as discussed above. Mixers (active or passive) may be used to assure proper mixing of the fluids involved in the flow through the microfluidic system 100. Mixers may be helpful, for example, to homogenate an analyte-reagent mixture.

The microscopic fluid samples acquired and separated according to the principles described herein may be analyzed as indicated above. Gaseous phase chromatography is commercially available as a MEM sensor chip from, for example, Agilent. Several types of physical sensors, including those mentioned above for measuring temperature, pressure, coefficient of viscosity, density, etc. can also be included. Chemical analyses can be achieved by titration and/or absorption spectroscopy as light is channeled to the microfluidic chip 114 (FIG. 3) by waveguides or fiber optics, and transmitted light can be collected and analyzed. Fluorescence of various components can also be detected.

Figure 6:
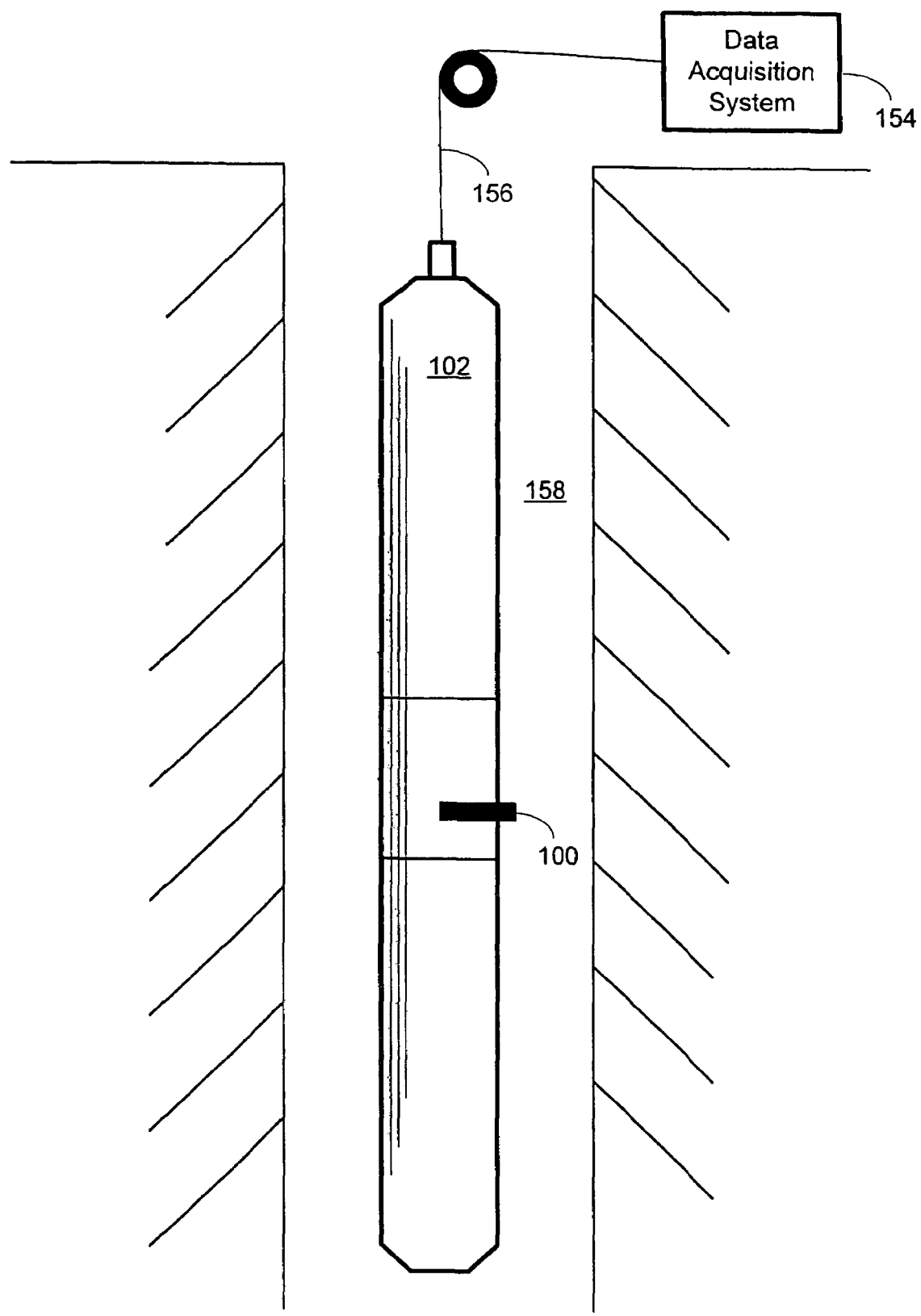
FIG. 6 is an illustration of one application of the present invention, useful for oilfield fluid monitoring and water management.

According to principles of the present invention, a component phase of interest such as liquid oil may be efficiently collected and tested remotely in a downhole environment or at the surface. Referring to FIG. 6, the drilling or sampling tool 102 may be lowered downhole and a stream of sample fluid containing a liquid of interest (such as liquid oil) flows across the microfluidic device 100. A separator of the microfluidic device 100 such as the porous membrane 108 (FIG. 1) or the microfabricated filter 128 (FIG. 5) separates the liquid of interest at the inlet 110 (FIG. 1) or elsewhere. The liquid of interest is channeled through the microfluidic device 100, and the liquid of interest may be further separated from gases by a second separator such as the microfabricated filter 128 (FIG. 3), or a secondary membrane embedded within the microfluidic system (e.g. FIGS. 7-8). The liquid of interest passes to a microfluidic analyzer such as the sample analysis section 126 (FIG. 3) of the microfluidic device 100. The sample analysis section 126 (FIG. 3) analyzes the liquid of interest and provides real-time or near real-time data ("near" indicating a small communication lag time) uphole to a data acquisition system 154 or operator via a communication medium 156. Alternatively, sample analysis results may be presented to lab personnel. The flow of sample fluids into the sample analysis section 126 (FIG. 3) may occur once, continuously, or at multiples depths in a wellbore 158. As mentioned above, the principles described herein may be used for surface analysis, wireline operations, production logging, logging/measurement while drilling, or other applications.

It will be understood by those of skill in the art having the benefit of this disclosure that the wireline configuration shown in FIG. 6 is exemplary in nature. Other suitable tools and configurations may also incorporate the principles of the present invention. For example, permanent monitoring installations, drilling tools, surface devices (for example to collect and analyze drilling mud samples), sample bottles, biological or chemical laboratory equipment, or other apparatus may include a microfluidic device with a separator according to the present invention.

Figure 7:
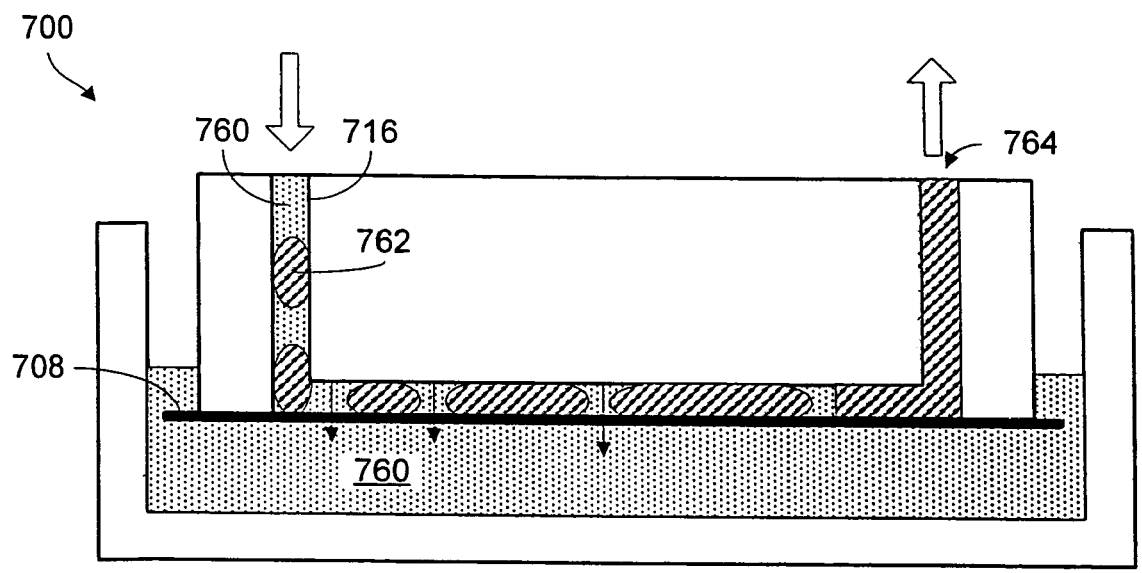
FIG. 7 is a representation of a microfluidic separator and method of separating according to another aspect of the present invention.

According to another embodiment of the invention illustrated in FIG. 7, there may be a microfluidic separator 700 with a membrane 708 disposed therein. The membrane 708 may be a secondary membrane in addition to the membrane 108 shown in FIG. 1. The microfluidic separator 700 includes a micro channel 716 through which a multi-phase mixture is introduced. The micro channel 716 is fabricated on or in contact with the membrane 708. The multi-phase mixture includes at least two immiscible fluids, shown in FIG. 7 as a first fluid 760 and a second fluid 762. The first fluid 760 is a membrane-wetting fluid that permeates through the membrane 708, where it is discarded. The second fluid 762 will not wet the membrane 708. Therefore, as the first liquid 760 permeates the membrane 708, it is eliminated, leaving only the pure nonwetting second fluid 762 being collected at an outlet 764 of the micro channel 716. The second fluid 762 may then be analyzed.

Figure 8:
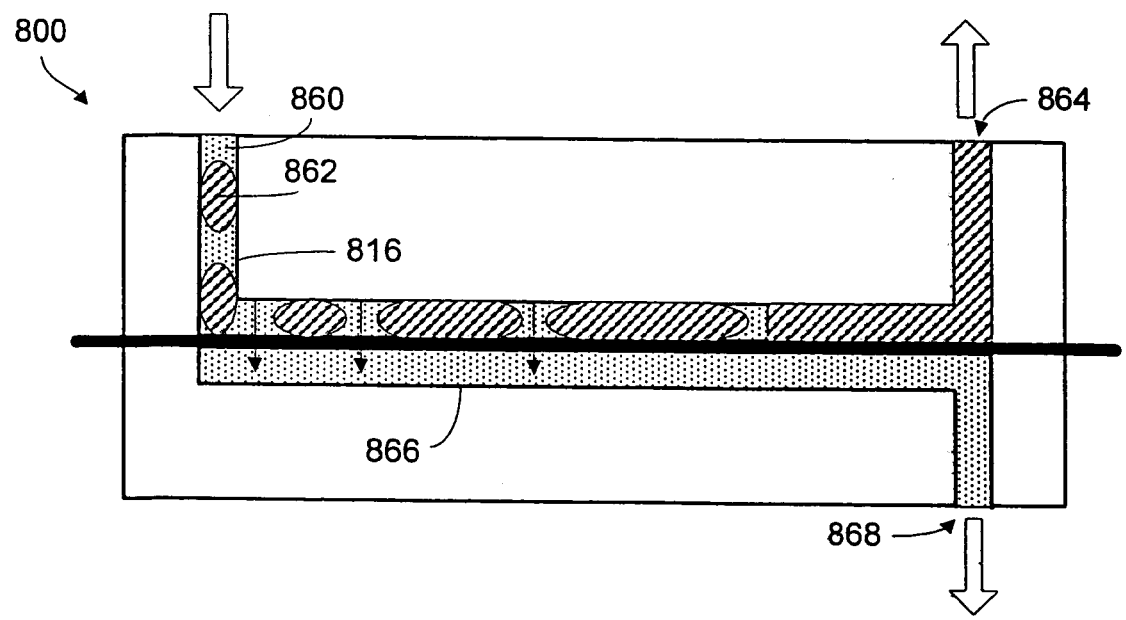
FIG. 8 is a representation of another microfluidic separator and method of separating that may enable analysis of multiple fluids of interest according to another aspect of the present invention.

Another embodiment similar to the embodiment of FIG. 7 is shown in FIG. 8. The embodiment of FIG. 8 is also microfluidic separator 800 with a membrane 808 disposed therein. The membrane 808 may be a secondary membrane. The microfluidic separator 800 includes a first micro channel 816 through which a multi-phase mixture is introduced. The first micro channel 816 is fabricated on or in contact with the membrane 808. The multi-phase mixture includes at least two immiscible fluids, shown in FIG. 8 as a first fluid 860 and a second fluid 862. The first fluid 860 is a membrane-wetting fluid that permeates through the membrane 808, where a pure sample thereof is collected by a second micro channel 866 that is in contact with an opposite side of the membrane 808. The first fluid 860 may exit the second micro channel 866 through an outlet 868 and be analyzed. The second fluid 862 is nonwetting to the membrane 808 and therefore a pure volume thereof remains in the first micro channel 816 and may exit through an outlet 864 for analysis as well.

While the invention has been described herein with reference to certain examples and embodiments, it will be evident that various modifications and changes may be made to the embodiments described above without departing from the scope and spirit of the invention as set forth in the claims.

What is claimed is:

1. An apparatus, comprising:
 a microfluidic device comprising a porous membrane for separating a multiphase mixture in a fluid flow stream within a structure wherein a pressure difference across the porous membrane is maintained below a capillary break-through pressure of a nonwetting fluid phase present in the multiphase mixture;
 wherein the porous membrane is arranged substantially tangent to an intended fluid flow direction of the multiphase mixture present in the fluid flow stream and disposed across a fluid sample inlet to the microfluidic device; and
 a microsieve structured and arranged adjacent to and downstream of the membrane and includes a capillary fluid separator having microfabricated channels arranged substantially tangent to the fluid stream downstream of the porous membrane.

2. An apparatus according to claim 1, wherein the structure is a submersible housing surrounding the microfluidic device.

3. An apparatus according to claim 1, wherein the membrane comprises one of: a water-repellant, oil-permeable membrane; an oil-repellent, water-permeable membrane; and an oil-and-water-repellent, gas-permeable membrane.

4. An apparatus according to claim 1, wherein the membrane comprises one of: PTFE, nylon, polyethylene, and polypropylene.

5. An apparatus according to claim 1, wherein the porous membrane is mechanically connected, adhesively connected, or chemically connected to the microsieve.

6. An apparatus according to claim 1, further comprising a downhole oilfield tool having a fluid flow stream, wherein the microfluidic device is disposed in the fluid flow stream and the porous membrane is arranged substantially tangent to a flow direction of the fluid flow stream.

7. An apparatus according to claim 1, wherein the microfluidic device comprises a sample manipulation/analysis module or chip.

8. An apparatus according to claim 1, wherein the microfabricated channels comprise pores of approximately 10 microns or less.

9. An apparatus according to claim 8, further comprising a secondary fluid outlet channel tangentially downstream of the capillary fluid separator.

10. An apparatus according to claim 1, wherein the multiphase fluid flow stream flows at a first flow rate and a separated fluid flow substream of at least one of the phases in the multiphase mixture flows through the microfluidic device at a second flowrate.

11. An apparatus according to claim 10, wherein the pressure difference across the membrane is maintained at a first pressure which ensures that the second flow rate of the separated fluid flow substream is one or more orders of magnitude lower than the first flow rate of the multiphase fluid flow stream, thus preventing the membrane from fouling without the need to backflush.

12. An apparatus according to claim 1, wherein the microsieve is in direct contact with the membrane thus providing a support structure for the membrane while simultaneously minimizing dead volume.

13. An apparatus according to claim 1, wherein the microsieve is made of a network of microchannels or a combination of a network or microchannels and a wire mesh or a network of microchannels and a perforated plate.

14. An apparatus according to claim 1, wherein the microsieve provides a support to the membrane and creates a uniform distribution of pressure over an entire area of the membrane.

15. A microfluidic system for performing fluid analysis, comprising:
- a submersible housing having a fluid analyzer and a power supply to provide power to said system;
- a substrate for receiving a multiphase mixture through a fluid sample inlet, wherein said substrate interconnects with said submersible housing; and
- a membrane disposed across the fluid sample inlet for separating a fluid of interest from the multiphase mixture; and
- wherein the substrate includes fabricated channels, such that the fabricated channels are arranged substantially tangent to the fluid stream downstream of the porous membrane.

16. An apparatus, comprising:
- a housing having a fluid flow stream, such that the housing is positioned in a downhole oilfield tool;
- a microfluidic device positioned in the housing comprising a porous membrane for separating a multiphase mixture in the fluid flow stream wherein a pressure difference across the porous membrane is maintained below a capillary break-through pressure of a nonwetting fluid phase present in the multiphase mixture;
- wherein the porous membrane is arranged substantially tangent to an intended fluid flow direction of the multiphase mixture present in the fluid flow stream; and
- a microsieve structured and arranged adjacent to and downstream of the porous membrane and includes a capillary fluid separator having microfabricated channels arranged substantially tangent to the fluid stream downstream of the porous membrane.

* * * * *